United States Patent [19]

Ghoshal et al.

[11] Patent Number: 5,741,715
[45] Date of Patent: Apr. 21, 1998

[54] QUINIDINE IMMUNOASSAY AND REAGENTS

[75] Inventors: Mitali Ghoshal, Neshanic Station, N.J.; Kathryn Sarah Schwenzer, Yardley, Pa.; Robert Sundoro Wu, West Orange, N.J.

[73] Assignee: Roche Diagnostic Systems, Inc., Branchburg, N.J.

[21] Appl. No.: 452,742

[22] Filed: May 30, 1995

[51] Int. Cl.$^6$ ............... G01N 33/542; G01N 33/577; G01N 33/533; C07K 16/44

[52] U.S. Cl. ............... 436/537; 436/546; 436/815; 530/388.9; 530/389.8; 530/807

[58] Field of Search ............... 546/177, 178; 530/389.8, 807, 388.9; 436/815, 822, 546, 537

[56] References Cited

U.S. PATENT DOCUMENTS

| | | |
|---|---|---|
| 4,045,420 | 8/1977 | Soffer et al. |
| 4,331,808 | 5/1982 | Buckler et al. ............... 562/456 |
| 4,420,568 | 12/1983 | Wang et al. ............... 436/536 |
| 4,585,862 | 4/1986 | Wang et al. ............... 544/319 |
| 4,668,640 | 5/1987 | Wang et al. ............... 436/537 |
| 5,097,097 | 3/1992 | Wang et al. ............... 544/207 |
| 5,492,841 | 2/1996 | Craig ............... 436/534 |

FOREIGN PATENT DOCUMENTS

| | | |
|---|---|---|
| 087564 | 7/1983 | European Pat. Off. |
| A-0 254 120 | 1/1988 | European Pat. Off. |
| A-0 279 213 | 8/1988 | European Pat. Off. |
| 85/00605 | 2/1985 | WIPO |
| WO-A-94 24559 | 10/1994 | WIPO |
| WO-A-95 03296 | 2/1995 | WIPO |

OTHER PUBLICATIONS

M. Wolff et al., Med. Chem. Res., vol. 1, pp. 101–108 (1991).

A. Soto et al., Clinical Chemistry, vol. 29, No. 6, pp. 1200–1201 (1983).

C. Regan, J. Pharm. Pharmacol., vol. 38, pp. 834–836 (1986).

A. Sidki et al., Cliin. Chem., vol. 33, No. 4, pp. 463–467 (1987).

Mattingly, P.G., Bioconjugate Chemistry, 3:430–431 (1992).

*Primary Examiner*—Mary E. Ceperley
*Attorney, Agent, or Firm*—George W. Johnston; Patricia S. Rocha-Tramaloni; Raina Semionow

[57] ABSTRACT

Novel quinidine derivatives are provided which can be used in an improved immunoasssay for the detection of quinidine and quinidine metabolites.

2 Claims, 9 Drawing Sheets

QUINIDINE IMMUNOASSAY AND REAGENTS

BACKGROUND OF THE INVENTION

The present invention relates to reagents used for the quantitative determination of quinidine in serum. In particular, the present invention relates to an improved fluorescence polarization immunoassay utilizing novel quinidine derivatives, as well as novel haptens, antibodies and tracers produced from said novel derivatives, as reagents in such assays.

Quinidine is a pharmaceutical agent generally prescribed for regulation of arrythmic heartbeat and thus its concentration in a patient's blood is critical and is carefully monitored during its administration. Serum quinidine levels of 1.5 to 5 mg/mL have been reported as therapeutic, based on nonspecific methodologies that measure quinidine metabolites as well as quinidine (Physician Desk Reference. 46th ed. Montvale, N.J.; Medical Economic Data; 1993:688–689). Quinidine was the first anti-arrhythmic for which the efficacy of therapeutic monitoring was demonstrated. The therapeutic concentration range for quinidine is quite narrow, and toxic effects due to overdosage can mimic symptoms of heart disease. The dosage required to achieve therapeutic serum levels is dependent on the drug formulation, patient age, severity and nature of the cardiac disorder and on individual variability in drug absorption and metabolism. Thus, monitoring of serum quinidine levels provides direct evidence to guide the physician in determining drug dosage for each individual patient.

The level of quinidine in serum samples can be determined through competitive binding immunoassays. Competitive binding immunoassays for measuring the concentration of an analyte (also referred to as a ligand) such as the drug quinidine, in a test sample are based on the competition between a ligand in a test sample and a labeled reagent, referred to as a tracer, for a limited number of receptor binding sites on antibodies specific to the ligand and tracer. The concentration of ligand in the sample determines the amount of tracer that will specifically bind to an antibody. The amount of tracer-antibody conjugate produced may be quantitatively measured and is inversely proportional to the quantity of ligand in the test sample.

Fluorescence polarization (FP) provides a quantitative means for measuring the amount of tracer-antibody conjugate produced in a competitive binding immunoassay. In general, fluorescent polarization techniques are based on the principle that a fluorescence labeled compound when excited by linearly polarized light will emit fluorescence having a degree of polarization inversely related to its rate of rotation. When a molecule, such as a tracer-antibody conjugate having a fluorescent label is excited with linearly polarized light, the emitted light remains highly polarized because the fluorophore is constrained from rotating between the time light is absorbed and emitted. When a "free" tracer compound (i.e. unbound to an antibody) is excited by linearly polarized light, its rotation is much faster than the corresponding tracer-antibody conjugate and the molecules are more randomly oriented, therefore the emitted light is depolarized.

In fluorescence polarization immunoassays (FPIA), fluorescence polarization is a reproducible function of the ligand or drug concentration, and thus is suitable for the quantitative determination of drug concentrations in serum for the purpose of therapeutic drug monitoring. When tracer, serum containing antibodies specific for the drug to be measured (for example, quinidine) and drug-free patient serum are mixed together, most of the tracer binds to the antibodies. As a result, when the bound tracer is excited with polarized light at 489 nm, the light emitted at 520 nm remains highly polarized. However, if drug is present in the patient sample, the drug will compete with the tracer for binding to the antibodies. Thus, more of the tracer will remain unbound and the emitted light is depolarized.

An FPIA according to the present invention can be any type of automated or manual FPIA. Preferably the FPIA is carried out on the automated COBAS FARA II® chemistry system (COBAS FP assay system, Roche Diagnostics, Inc., Somerville, N.J.) to measure the binding of fluorescein labeled drug (tracer) to specific antibodies (see Dandliker and Feigen, Biochem. Biophys. Res. Comm. 5: 299, 1961).

The COBAS FP assay system measures the fluorescence polarization resulting from the interaction of fluorescein labelled tracer, antibody and calibrators containing known amounts of drug, such as quinidine, in human serum. From the measurements a curve relating drug concentration to millipolarization (mP) units is produced. The precision of drug concentration measurement is related to dynamic span of the standard curve and relative intensity of the tracer in solution. When a maximum amount of tracer is bound to the antibody in the absence of drug in the serum, maximum polarization in mP units is measured. "Span" (also known as "dynamic curve span") indicates the difference between the minimum and maximum millipolarization units produced by tracer bound to antibody. A larger span indicates better precision and sensitivity of tracer performance. "Intensity" is a measure of the strength of the fluorescence signal above the intensity of the background fluorescence. Intensity of a tracer preferably remains constant throughout the life of the reagent. Free tracer depolarizes light yielding 20–75 mP. A good dynamic span ranges from 150–250 mP.

Subsequently, the tracer, antibody and patient's serum are allowed to interact under the same conditions which generated the calibration curve. The mP units thus obtained can be correlated accurately to the drug level in the patient's serum by comparison with the calibration curve in the assay.

Fluorescein-labeled quinidine compounds are known, for example 5-aminofluorescein-labeled quinidine (see U.S. Pat. No. 4,585,862), DTAF-labeled quinidine (see U.S. Pat. No. 4,420,568), β-galactosyl-umbelliferone-labeled quinidine (see EP 83100413.0) and enzyme labeled quinidine (see WO 85/00605). However, some of these compounds contain types of linkages that are susceptible to hydrolysis, therefore shortening the shelf life of the tracers, for example carbamate ester and O-triazinyl ether linkages in quinidine tracers derived out of the C-9 position of quinidine (see U.S. Pat. Nos. 4,420,568 and 4,585,862).

A method to prepare quinidine derivatives out of the C-6 position on the quinidine molecule has been described for making an enzyme labeled-quinidine using N-succinimidyl 3-(2-pyriyldithio)propionate (SPDP) (see WO 85/00605), but not for making fluorescein-labeled quinidine tracers. This method produces a dialkylkated product out of the C-6 position in the quiniclidine molecule which results in an unstable tracer due to the positive charge at the quiniclidine ring prone to hydrolytic cleavage.

Therefore, it is an object of the present invention to provide a stable quinidine derivative substituted exclusively at the 6 position of the quinidine molecule.

It is a further object of the present invention to provide a stable fluorescein tracers derived from 6-substituted quinidine derivatives having an amide linkage between the fluorescein molecule and the quinidine derivative.

An additional object of the present invention is to provide reagents, such as antibodies, derived form the quinidine derivatives for an improved fluorescence immunoassay to quantitate quinidine in body fluid samples.

SUMMARY OF THE INVENTION

The present invention relates to novel quinidine derivatives of the formula

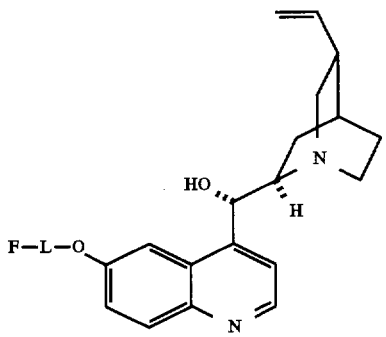

wherein L is a linking group consisting of from 1 to 10 carbon atoms, which may be straight or branched chain, and may be saturated or unsaturated, and may include from 0–3 heteroatoms. F is a functional group selected from the groups consisting of amino, carboxyl, sulhydryl, imino, and maleimide.

The compounds of formula I are useful as haptens in the preparation of immunogens as well as useful to prepare labelled quinidine tracers.

The invention also relates to antibodies produced against the novel quinidine derivatives of the present invention. The invention further relates to a kit containing the reagents of the present invention for performing an improved fluorescence polarization immunoassay.

BRIEF DESCRIPTION OF THE FIGURES

The present invention may be more readily understood by reference to the following figures. The numbers following the compounds correlate to numbers shown in the figures.

DETAILED DESCRIPTION OF THE INVENTION

Figure 1:
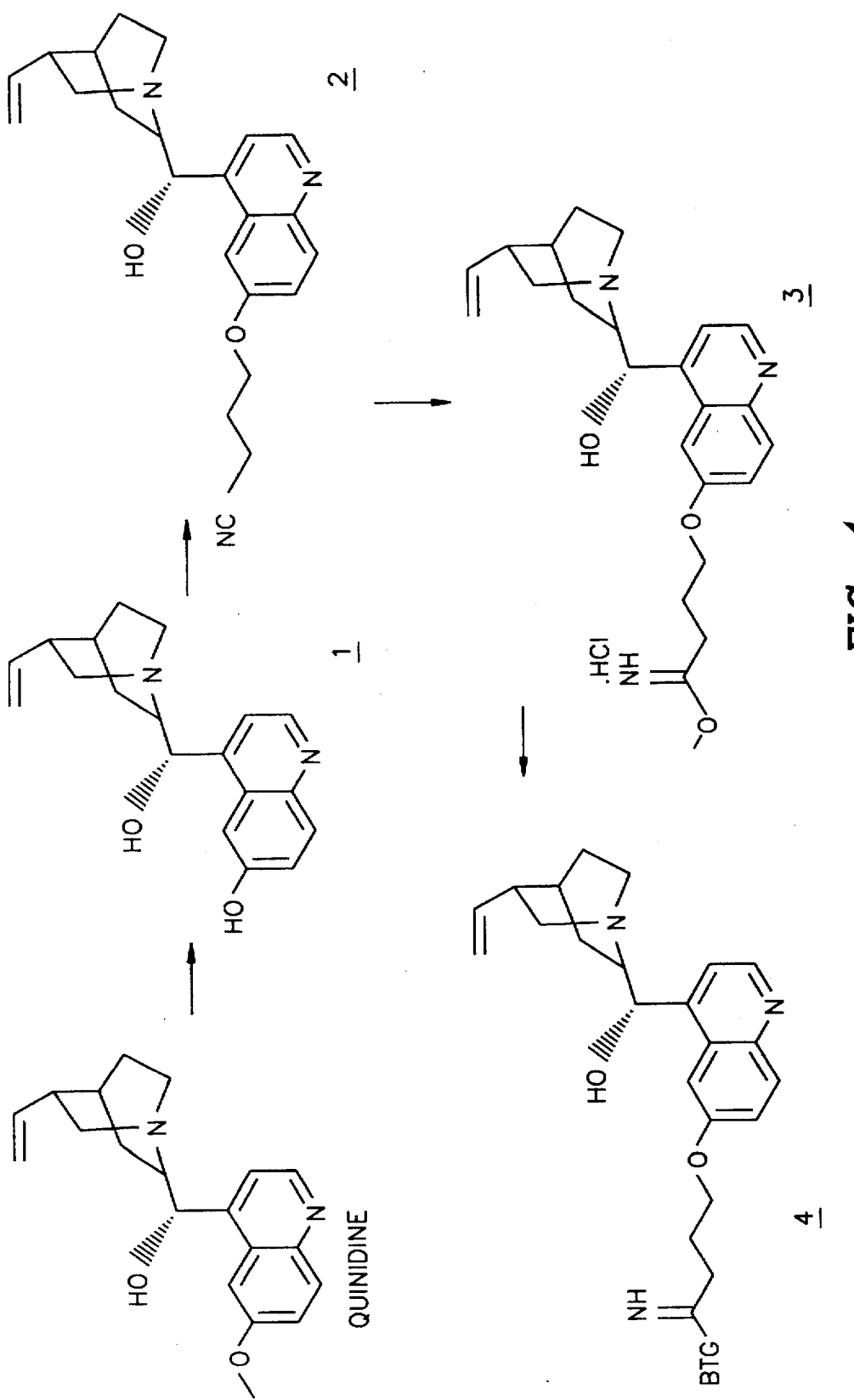
FIG. 1 shows the formulae of the starting materials and intermediates involved in the synthesis of (9S)-4-[(9-hydroxycinchonan-6'yl)oxy]-1-iminobutyl-[BTG] (4)

The present invention relates to novel quinidine derivatives of the formula

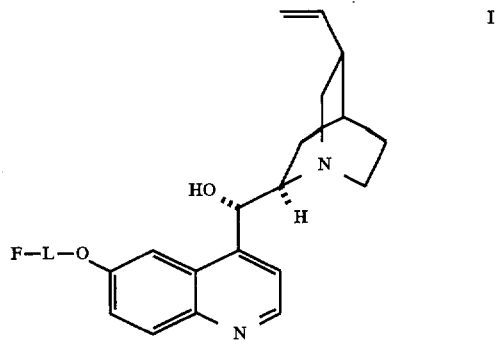

wherein L is a linking group consisting of from 1 to 10 carbon atoms, which may be straight or branched chain, and may be saturated or unsaturated, and may include one or more aromatic groups and may include 0–3 heteroatoms. Linking groups are well known to those of skill in the art (see e.g. U.S. Pat. No. 4,160,016). F is a functional group selected from amino, carboxy, sulfhydryl, imino, and maleimide. The meaning of the term "functional groups" is apparent to those of skill in the art.

Preferably L is from 1–5 carbon atoms. Preferably the carbon atoms are unsaturated and the unsaturated group includes an aromatic group such as phenyl. Preferably the heteratoms include O, N, and S. F is most preferably carboxyl or amino.

The novel quinidine derivatives of the present invention are used for preparing antibodies to quinidine and quinidine derivatives, as well as for bonding to detector molecules to form tracers for use in fluorescent polarization assays for the detection of quinidine in body fluid samples.

The present invention provides a quinidine derived hapten. A hapten is a compound capable of eliciting an immune response in a challenged animal in order to generate antibodies against the compound, e.g. a quinidine derivative, for use in an FPIA. An antibody used in the quinidine FPIA preferably is specific for quinidine and will not react with quinidine-like compounds such as quinine (shown below).

The hapten used to prepare the preferred immunogen of the present invention was derivatized at the C-6' position on the quinidine molecule.

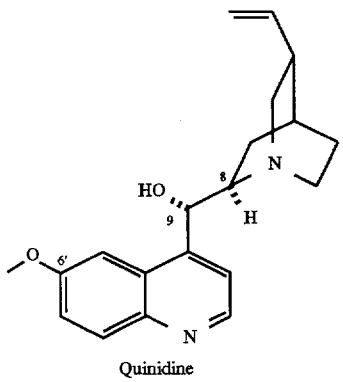

Quinidine

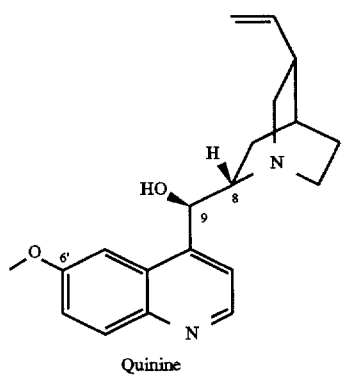

Quinine

An alkyl group is attached at the C-6' position of quinidine to introduce a spacer. The preferred amount of alkylating reagent used to prepare the hapten and other quinidine derivatives of the present invention is one molar equivalent, the most preferred amount being less than one molar equivalent.

The hapten is used to prepare an immunogen- a conjugate of the hapten and a protein carrier molecule- to elicit an antibody response. An immunogenic carrier molecule is a macromolecule capable of independently eliciting an immunological response in a host animal and which can be coupled to a quinidine derivative of the present invention. Suitable immunogenic carrier molecules are protein carriers which include bovine serum albumin (BSA), keyhole limphet hemocyanin (KLH) polypeptides and bovine thyroglobulin (BTG).

The structure of the immunogen of the present invention is as follows:

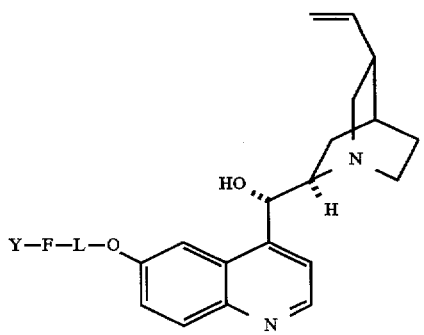

II wherein L is a linking group consisting of from 1 to 10 straight or branched chain, saturated or unsaturated carbon atoms; preferably of from 1–5 carbon atoms. Preferably the carbons are unsaturated and include at least one aromatic group such as phenyl. L may also include 0–3 heteroatoms selected from O, N and S. F is a functional group selected from amino, carboxyl, sulfhydryl, imino, and maleimide. F is most preferably carboxyl or amino. Y is an immunogenic carrier molecule such as a protein; a polysaccharide such as dextran or an oligosugar; or a naturally occuring or synthetic polyaminocarboxylic acid such as polylysine or polyglycine.

A preferred immunogen of the present invention is illustrated by the formula

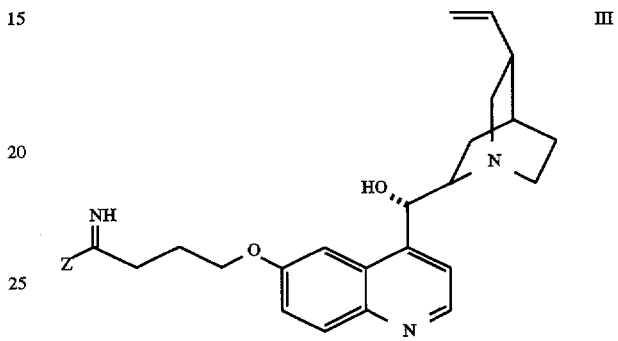

III wherein Z is a protein carrier. Z can include albumin, bovine serum albumin (BSA), key-hole limpet hemocyanin (KLH), bovine thyroglobulin (BTG), egg ovalbumin, bovine gamma globulin, small natural polypeptides such as gramicidin, and various synthetic polypeptides. The preferred immunogen of the present invention contains an imino as the functional group F and BTG as the protein carrier Z. A preferred host animal for production of the antibody includes mice.

The preferred quinidine immunogen is prepared from a hapten bearing a mono-substituted imidate ester wherein L is 3 carbon atoms. The process for making the quinidine immunogen of the present invention is shown in FIG. 1 and detailed in examples 1,2,3 and 7. The first step is the demethylation of quinidine to yield 6-hydroxycinchonine (1) according to known methods (see L. D. Small, et al., J. Med. Chem. vol. 22, 1014–1016, 1979). The second step is alkylation of 6-hydroxyquinidine(1) to (9S)-4-[(9-Hydroxycinchonan-6'yl)oxy]butanenitrile (2). Alkylating agents that can be used include 4-bromobutyronitrile, chloroacetonitrile, 3-chloropropionitrile, and 3-(bromomethyl) benzonitrile. The preparation of derivatives wherein L is less than 4 is given in Examples 4, 5 and 12; derivatives wherein L contains phenyl in Example 6.

The preferred amount of alkylating reagent used is one molar equivalent of, for example 4-bromobutyronitrile. Most preferably used is 0.9 molar equivalent of alkylating reagent. Compound (2) is the preferred compound of the present invention used to generate the preferred monoclonal antibody Q6-6C5 (MoAb Q6-6C5).

In contrast, the use of more than one molar equivalent of alkylating reagent results in disubstituted quinidine derivatives, shown below.

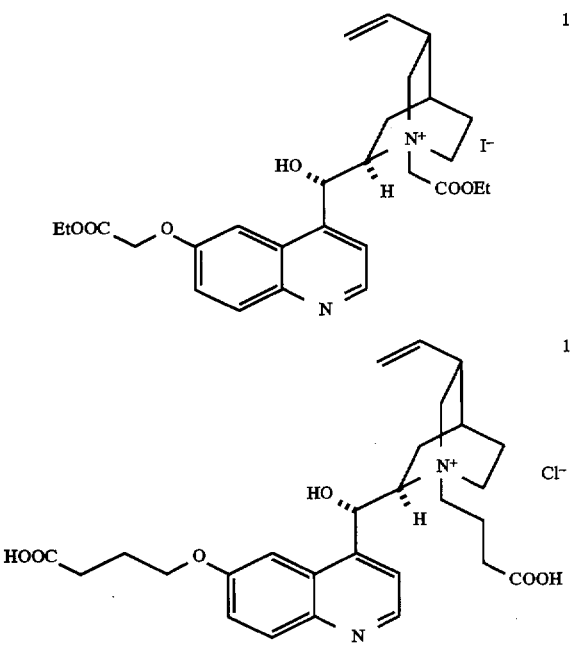

The syntheses of the above undesirable compounds, (S)-8-Ethenyl-2-[hydroxy-6-(2-ethoxy-2-oxoethoxy)-4-quinolinylmethyl]-1-(2-ethoxy-2-oxoethyl)azoniabicyclo[2.2.2]octane iodide (15) and (9S)-1-(3-carboxypropyl)-6'-(3-carboxypropoxy) cinchoninum chloride (16) using two molar equivalents of alkylating reagent are described in Examples 9 and 10.

The third step of the immunogen synthesis is converting the nitrile on the hapten to an imidate ester for subsequent coupling of the hapten to a protein. The use of imidate ester containing molecules for coupling to proteins' is known, for example, using a cross-linking reagent such as dimethyl-suberimidate dihydrochloride (Pierce). The use of this cross-linker, however, can result in polymerization of the proteins causing the precipitation of the hapten conjugate. Also known is the reaction of an imidate ester with an amine to form amidine. It is preferable, however, in the present invention to have a monofunctionalized active group, i.e. an imidate ester, directly on the hapten for the most effective protein coupling.

A monofunctionalized imidate ester derivative of cocaine has been used to make a cocaine immunogen (see U.S. Pat. No. 4,045,420). Sodium methoxide in methanol was used to convert the nitrile to benzoyl ecgonine bearing an imidate ester for protein coupling. This method, however, is not suitable for preparing the quinidine immunogen of the present invention due to the presence of the C-9 hydroxy group on the molecule which is capable of crossreacting with the imidate ester as soon as it is formed.

A preferred method of making the immunogen of the present invention, therefore, is through an acid catalyzed reaction. The imidate ester is generated by treatment of the nitrile with HCl in methanol. The resulting imidate ester forms a hydrochloride salt with amino groups on the molecule. The imidate ester is preferably used for protein coupling soon after it is made. In the preferred embodiment compound (2) is treated with hydrochloric acid gas in methanol to form (9S)-4-[(9-hydroxycinchonan-6'-yl)butanimidic acid methyl ester (3).

Alternate methods to prepare the quinidine hapten include forming a hapten conjugate wherein the functional group F is carboxy. Typically used is the direct coupling of a carboxyl group to an amine using carbodiimide. An alkylating agent is attached to the hydroxyl group of cinchonine (see example 12). The carboxy end is activated at the hydroxyl using DCC (dicyclohexyl carbodiimide) and NHS (N-hydroxysuccinimide) to form the active ester. The active group couples to a protein carrier under relatively mild reaction conditions (see U.S. Pat. Nos. 5,101,015 and 4,329,281).

Also widely used are sulfhydryl reactive maleimide- or α-haloacetamide-linker, known to react selectively with thiols to form thioether-linked conjugates. A hapten conjugate wherein the functional group F is a maleimido group can be linked to proteins bearing sulhydryl groups (see example 18). The amine reacts with the maleimido derivative for effective coupling to another molecule bearing sulfhydryl residues. Maleimido-NHS active ester compounds are commercially available as bifunctional linkers, such as succinimidyl 4-(p-maleimidomethyl)cyclohexane-1-carboxylate (SMCC), m-maleimidobenzoyl-N-hydroxysuccinimide ester (MBS), succinimidyl 4-(p-maleimidophenyl)butyrate (SMPB), and derivatives thereof.

Bifunctional linkers, such as SPDP, may also be used to link the hapten and protein together to form a disulfide-containing conjugate. However, the preparation of either the thioether-linked or the disulfide-linked conjugates is a multistep procedure, whereas the coupling of carboxyl groups to proteins is a more direct procedure.

The quinidine immunogens of the present invention were used to generate polyclonal and monoclonal antibodies, for example the novel monoclonal antibody MoAb Q6-6C5 and polyclonal antibody P796. The use of the novel monoclonal antibody in conjunction with the novel tracers of the present invention (described below), results in an improved immunoassay for the detection and quantitation of quinidine.

For the preferred antibody of the present invention cross reactivity should not exceed, for the following quinidine metabolite compounds: quinidine-N-Oxide 13.5%: 3-S-hydroxyquinidine 11%; 2'-oxoquinidine 3%: O-desmethylquinidine 43.5%. The preferred monoclonal Ab also has dynamic curve span of at least 150 mP.

Figure 5:
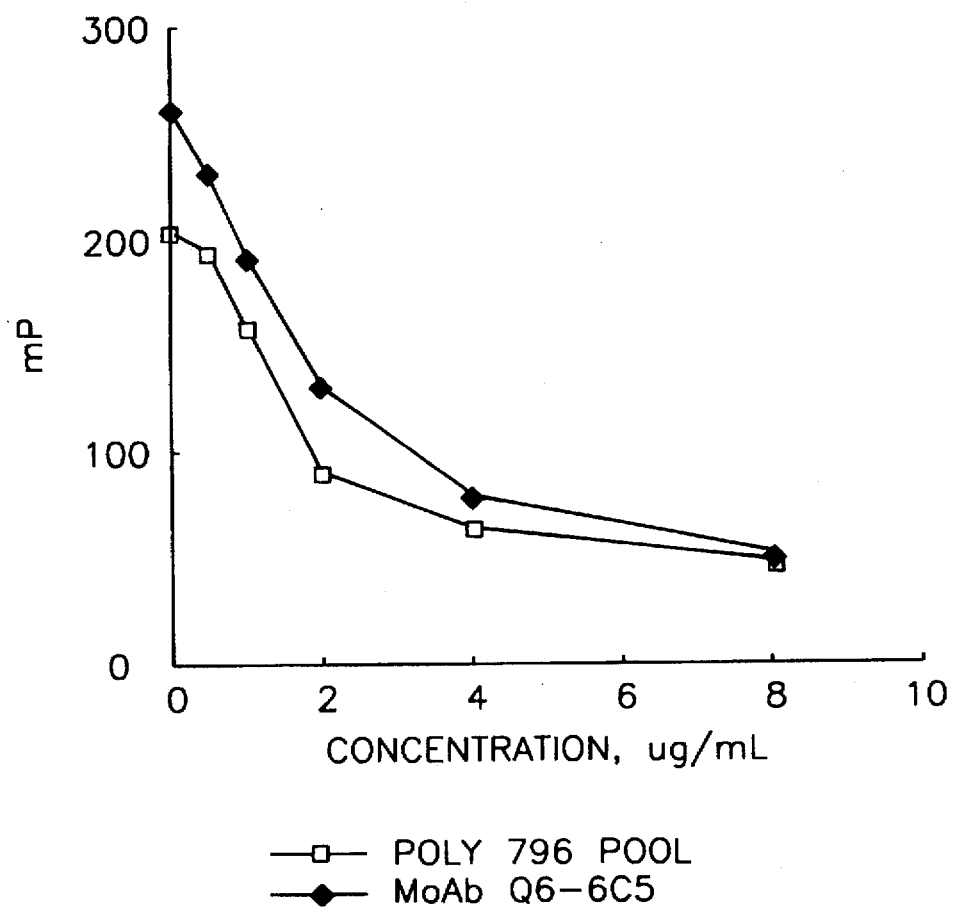
FIG. 5 shows comparison testing of monoclonal antibody MoAb Q6-6C5 and polyclonal antibody 796 binding to the tracer (9S)-N-[(3',6'-Dihydroxy-3-oxospiro[isobenzofuran-1(3H),9'-[9H]xanthen]-5yl) methyl]-4-[(9-hydroxycinchonan-6'yl)oxy]butamide (7)

The antibodies were tested to determine their efficiency in binding a new tracer of the present invention. FIG. 5 shows the comparison between using the polyclonal antibody and the monoclonal antibody with the tracer of the present invention in the FPIA. Both antibodies demonstrate binding to the tracer. The curves indicate that the monoclonal antibody has a larger dynamic span and therefore increased sensitivity in the FPIA.

Table 1 shows the cross-reactivity of MoAb Q6-6C5 towards various metabolites of quinidine including quinine as determined in the FPIA. Cross reactivity with quinine is shown to be insignificant, therefore quinine will not interfere with the performance of the quinidine assay. MoAb Q6-6C5 demonstrates lower cross-reactivity to the metabolites (with the exception of dihydroquinidine) thus providing a more precise and highly specific method for monitoring quinidine in serum. These results were obtained using an assay protocol such as the one described in Example 22.

TABLE 1

CROSS REACTIVITY

| Test Compound | Concentration of Test Compound Added (ug/mL) | New Kit using MoAbQ6-6C5 & Tracer 7 % Cross-Reactivity | Current Kit using Tracer 14 % Cross-Reactivity | TDx % Cross-Reactivity |
|---|---|---|---|---|
| Quinidine-N-Oxide | 10 | 13.5 | 30.5 | 31.9 |
|  | 100 | 4.9 | H | 7.2 |
| 3-S-Hydroxyquinidine | 10 | 11 | 21 | 18.8 |
|  | 100 | 3.7 | 4.3 | 5.3 |
| 2'-Oxoquinidine | 10 | 3 | 20 | 3.3 |
|  | 100 | 1 | 3.7 | 1.1 |
|  | 500 | 0.53 | 1.55 | 0.58 |
|  | 1000 | 0.35 | H | 0.39 |
| O-Desmethylquinidine | 1 | 55 | 55 | 206 |
|  | 10 | 43.5 | 46.5 | 60.3 |
| Dihydroquinidine | 10 | H | 67 | 79 |
|  | 5 | 160 | 76 | 88 |
|  | 2.5 | 156 | 76 | 96 |
| 10,11-Dihydro quinidine-diol | 10 | 1 | 14.5 | 3.9 |
|  | 100 | 1.7 | 3.2 | 1.8 |
| Quinine | 10 | <0.1 |  | not tested |
|  | 100 | <0.1 | <0.1 | 0.8 |
|  | 1000 | <0.1 |  | not tested |

H: High

The present invention also provides novel quinidine-derived fluorescein labelled tracers for use in fluorescent polarization immunoassays. Fluorescein compounds are known in the art (Molecular Probes Publication, Eugene, Oreg.; Bioconjugate Chemistry, 1192, 3, 430–431, 1992; U.S. Pat. No. 4,668,640) and have been utilized to make fluorescein-labeled quinidines, for example 5-aminofluorescein-labeled quinidine (see U.S. Pat. No. 4,585,862), DTAF-labeled quinidine (see U.S. Pat. No. 4,420,568), β-galactosylumbelliferone-labeled quinidine (see EP 83100413.0) and enzyme labeled quinidine (see WO 85/00605).

Known fluorescein-labeled quinidines are derived from the C-9 position of the quinidine molecule and contain linker arms of carbamate ester and O-triazinyl ether (see U.S. Pat. Nos. 4,420,568 and 4,585,862). However, these types of known linkages are susceptible to hydrolysis and therefore not suitable for making the fluorescein tracer of the present invention.

Another commercially available fluorescein labelled tracer, ((3',6'-dihydroxy-3-oxospiro(isobenzofuran-1(3H), 9'-(9H)xanthen-5-yl)amino)-2-oxoethyl)-2-(hydroxy(6-(2-ethoxy-2-oxoethoxy)-4-quinolineyl)methyl)-1-azoniabicyclo(2.2.2)octane chloride hydrochloride (14), bears a positive charge on the quinuclidine ring (shown below), causing instability of the compound.

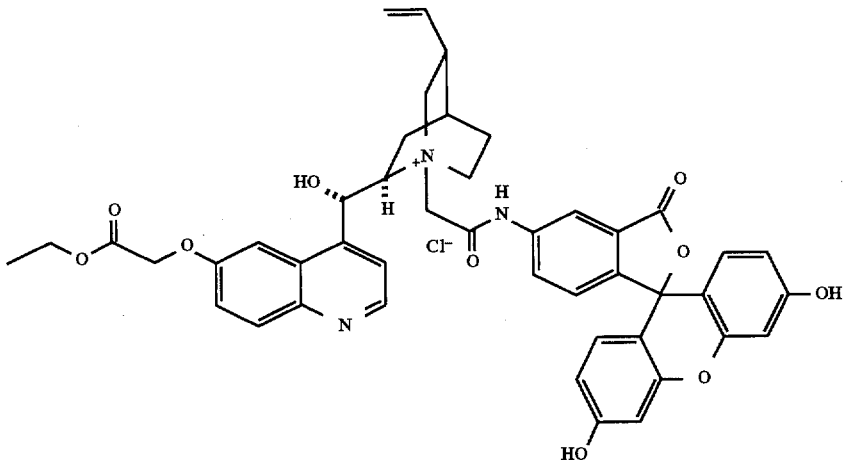

14

The structure of the fluorescence polarization tracer of the present invention is represented by the formula

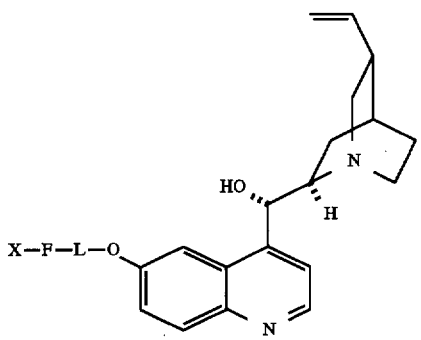

IV wherein L and F are as previously defined. X is a detector molecule selected from the group consisting of a chemiluminescent, such as luciferin, umbelliferone and napthalene-1,2-dicarboxylic acidhydrazide (U.S. Pat. No. 4,331,808); an energy donor molecule, such as a fluorescein "Q" as defined below or Texas Red; and a radiolabelled group such as $I^{125}$-tyramine, $C^{14}$ labelled compounds, such as methyl iodide or amino acids.

The preferred tracer of the present invention has the formula

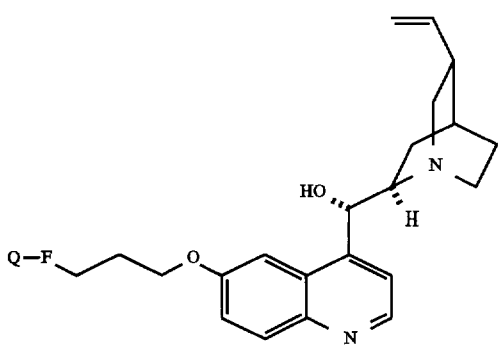

V wherein F is selected from amino or carboxy and Q is a fluorescence emitting compound such as 5-carboxyfluorescein, 6-carboxyfluorescein, 5-aminofluorescein, 6-aminofluorescein, 5-fluorescein isothiocyanate, 6-fluorescein isothiocyanate, 4'-aminomethylfluorescein, 5-aminomethylfluorescein and derivatives of aminofluorescein, e.g. glycinated fluorescein. Most preferred are aminomethyl fluorescein and carboxyfluorescein.

The group Q may be selected from a variety of commercially available detector molecules (Molecular Probes, Inc. Eugene, Oreg.) and attached to the quinidine derivatives by methods known in the art to provide reagents useful in different assay formats. In addition to fluorescein, detector molecules such as radiolabels or chemiluminescent detector molecules, for example. tyramine can also be used.

Figure 2:
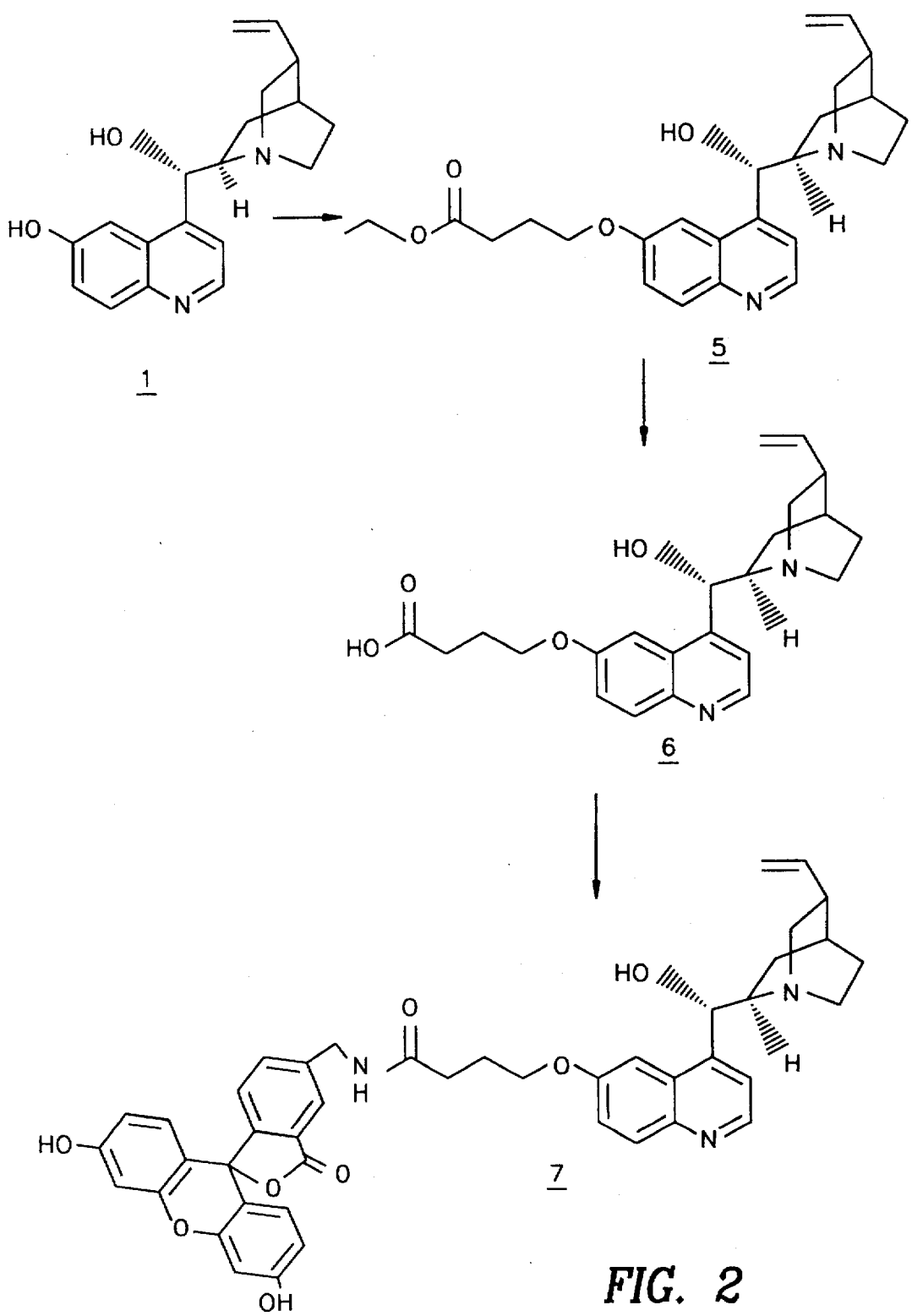
FIG. 2 shows the formulae of the starting materials and intermediates involved in the synthesis of (9S)-N-[(3',6'-Dihydroxy-3-oxospiro[isobenzofuran-1(3H),9'-[9H]xanthen]-5yl) methyl]-4-[(9-hydroxycinchonan-6'-yl)oxy] butamide (7)

FIG. 2 illustrates the method for preparing the most preferred novel FP tracer of the present invention (9S)-N-[(3',6'-Dihydroxy-3-oxospiro [isobenzofuran-1(3H),9'-[9H] xanthen]-5yl) methyl]-4-[(9-hydroxycinchonan-6'-yl)oxy] butamide (7). The synthesis of this tracer is described in examples 11-13.

The first step in the synthesis of the tracer of the present invention, as for the hapten. is the alkylation of 6-hydroxyquinidine using preferably one or less molar equivalent of alkylating reagent. The first step is the alkylation of 6-hydroxyquinidine(1) to (9S)-4-[(9-Hydroxycinchonan-6'-yl) oxybutanoic acid ethyl ester (5) using one molar equivalent of ethyl 4-bromobutyrate, most preferably using 0.9 molar equivalent of ethyl 4-bromobutyrate. The alkylated product (5) is hydrolyzed to obtain the corresponding acid (9S)-4-[9-Hydroxycinchonan-6'-yl)oxybutanoic acid (6). The acid is activated to form N-hydroxysuccinimide using a method well-known in the literature. This activated ester is coupled with 5-aminomethylfluorescein in the presence of pyridine to give the quinidine tracer (9S)-N-[(3',6'-dihydroxy-3-oxospiro[isobenzofuran-1(3H),9'-[9H]xanthen]-5yl) methyl]-4-[(9-hydroxycinchonan-6'-yl)oxy]butamide (7).

The linkage between the antigenic moiety and the fluorescent moiety in the tracer can be an amidine linkage as in the novel hapten structure. However, the linkage between the antigenic quinidine moiety and the fluorescein molecule in the tracer is preferably different from the amidine linkage used to prepare the immunogen. Linkages to be used to form the tracer can include amide, urea, thiourea, amidine, ether, and thioether. The preferred linkage for the tracer in the present invention is an amide bond which provides more stability to the tracer.

Figure 6:
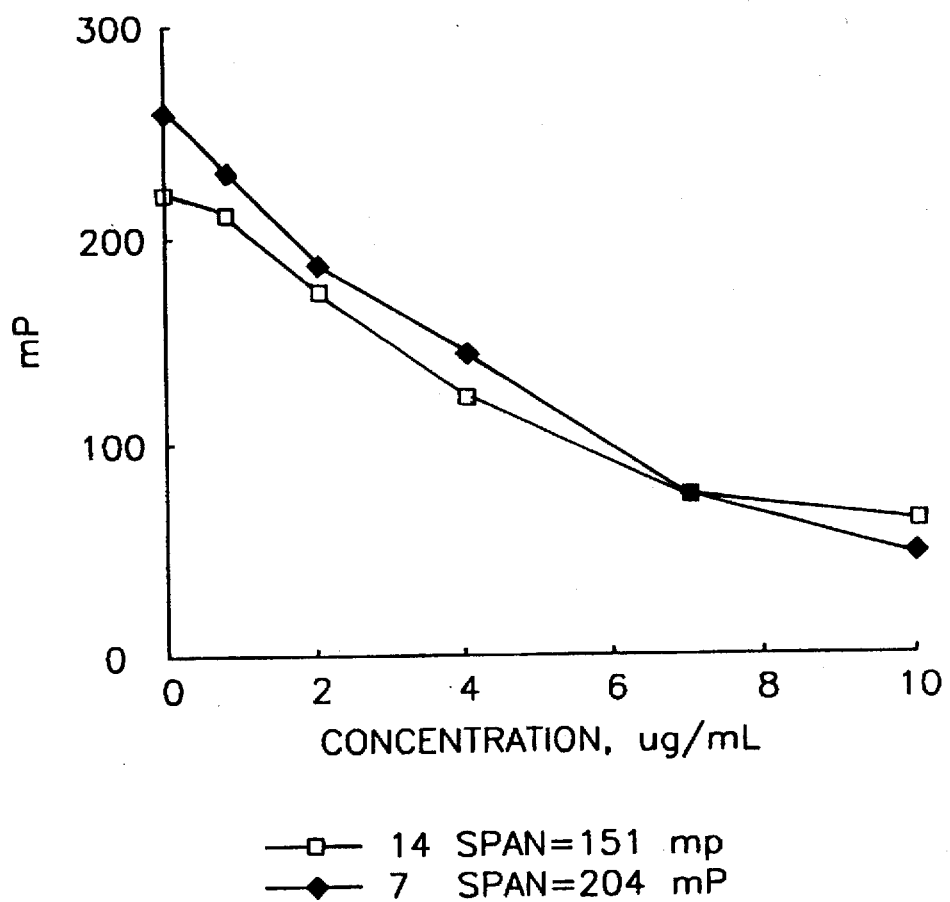
FIG. 6 shows the comparison testing of monoclonal antibody MoAb Q6-6C5 with the tracer (2(S)-exo,syn)-8-ethenyl-1-(2-((3',6'-dihydroxy-3-oxospiro(isobenzofuran-1(3H),9'-(9H)xanthen-5-yl)amino)-2-oxoethyl)-2-(hydroxy (6-(2-ethoxy-2-oxoethoxy) -4-quinolineyl)methyl)-1-azoniabicyclo(2.2.2)octane chloride hydrochloride (14), and the tracer (9S)-N-[(3',6'-Dihydroxy-3-oxospiro [isobenzofuran-1(3H),9'-[9H]xanthen]-5yl) methyl]-4-[(9-hydroxycinchonan-6'-yl)oxy]butamide (7) formulations.
Figure 7:
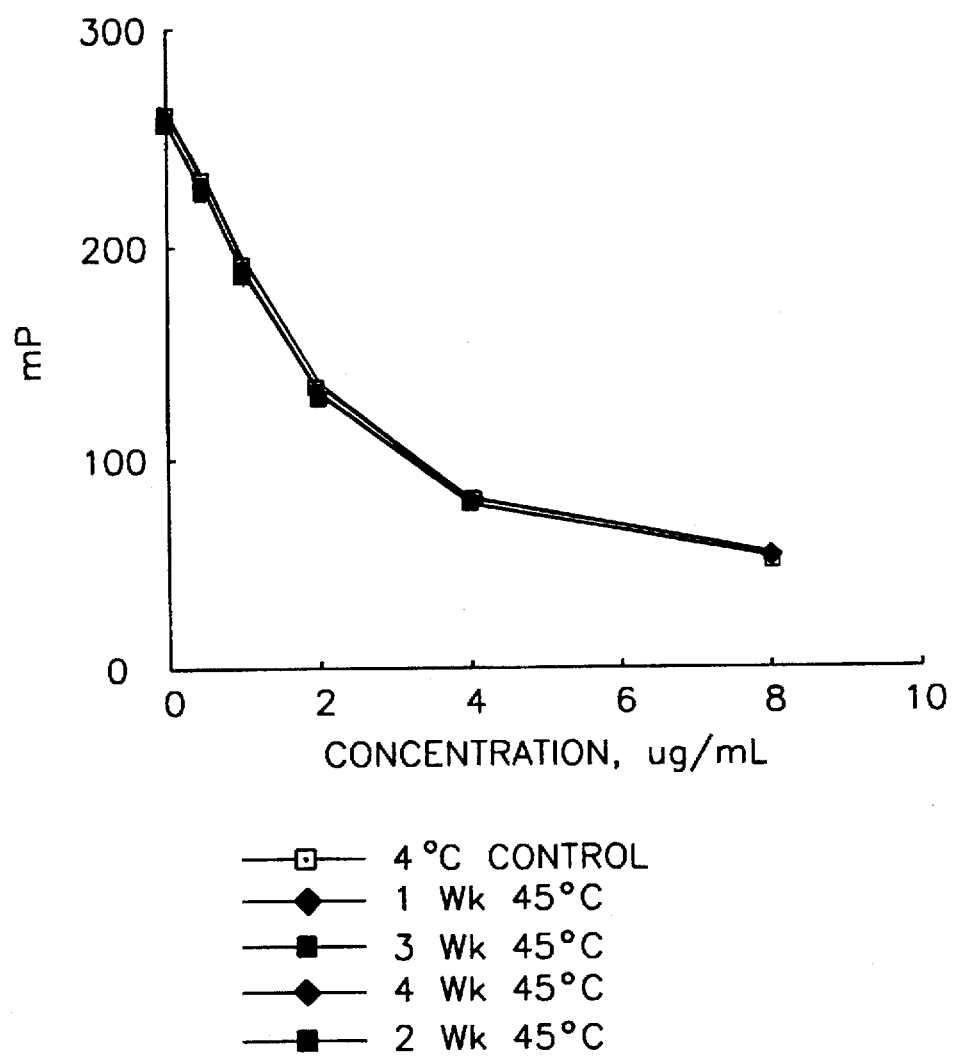
FIG. 7 shows the stability of the tracer (9S)-N-[(3',6'-dihydroxy-3-oxospiro[isobenzofuran-1(3H),9'-[9H]xanthen]-5yl) methyl]-4-[(9-hydroxycinchonan-6'-yl)oxy] butamide (7) incubated at 45° C.
Figure 8:
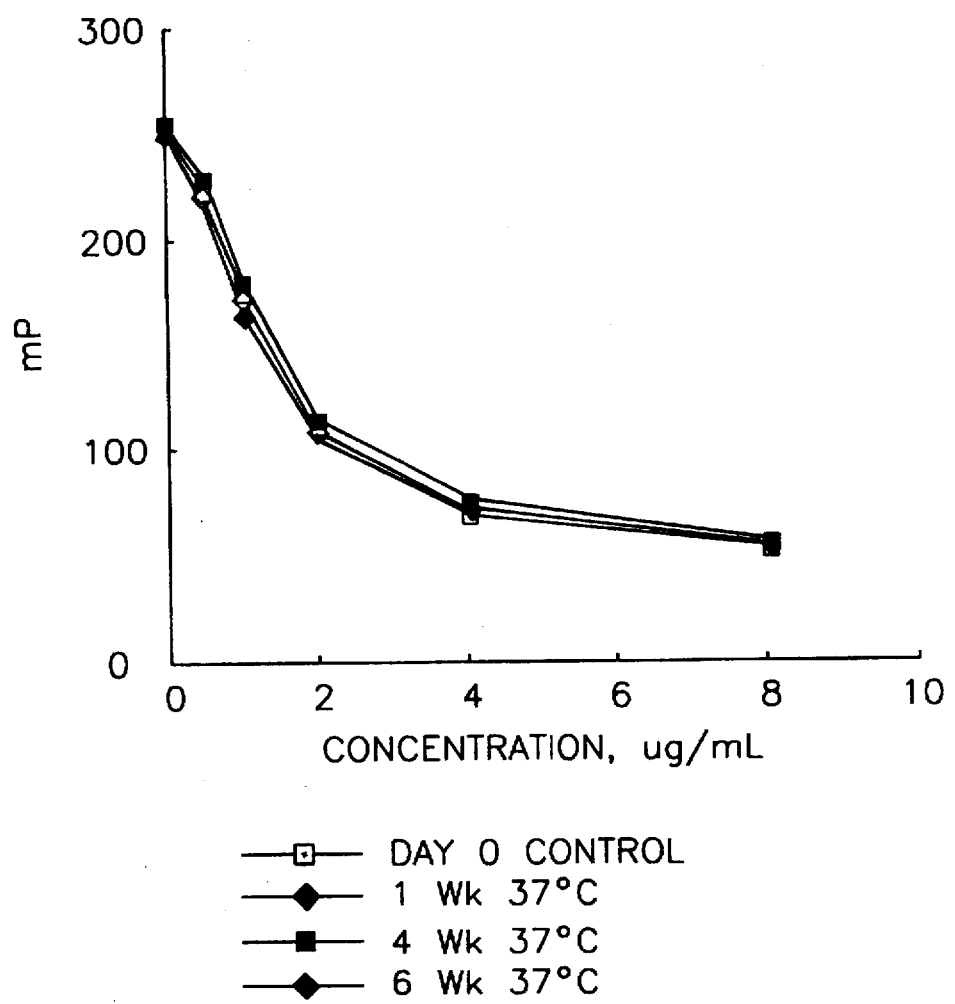
FIG. 8 shows the stability of the tracer (9S)-N-[(3',6'-dihydroxy-3-oxospiro[isobenzofuran-1(3H),9'-[9H]xanthen]-5yl) methyl]-4-[(9-hydroxycinchonan-6'-yl)oxy] butamide (7) incubated at 37° C.
Figure 9:
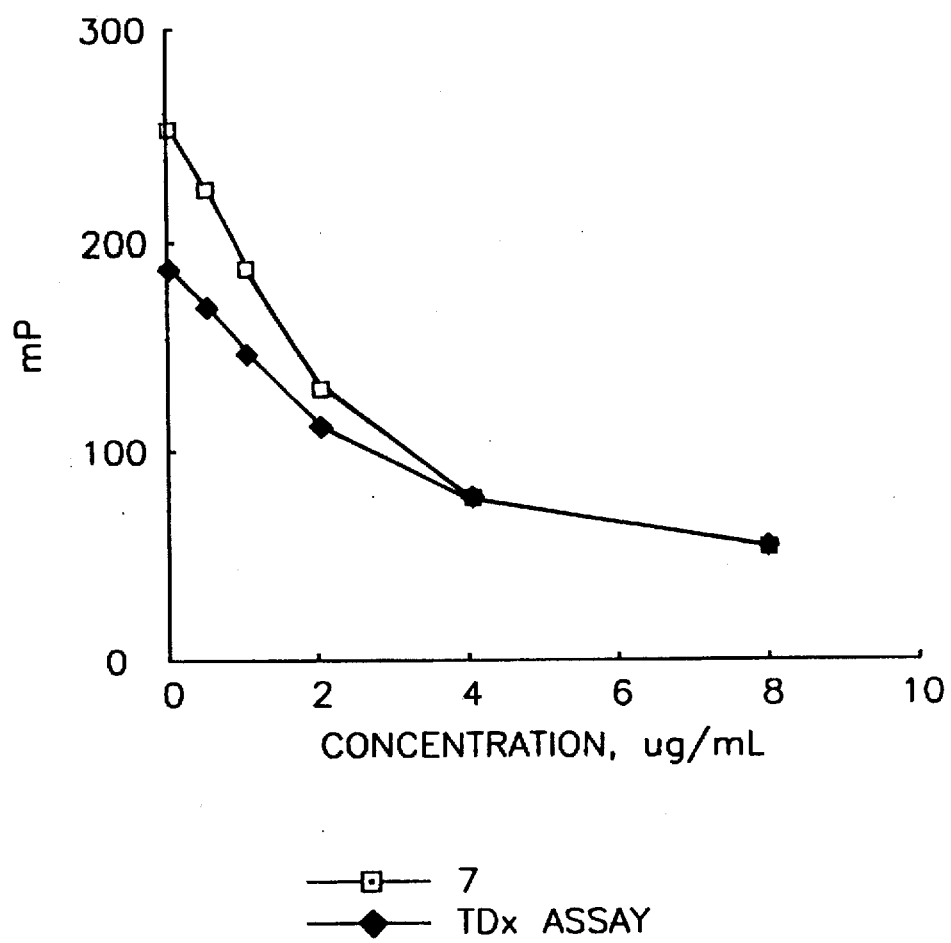
FIG. 9 shows the comparison of the dynamic span in an FPIA using the novel tracer (9S)-N-[(3',6'-dihydroxy-3-oxospiro[isobenzofuran-1(3H),9'-[9H]xanthen]-5yl) methyl]-4-[(9-hydroxycinchonan-6'-yl)oxy]butamide (7) and MoAb Q6-6C5 and a commercially available reagent system.

The new tracer (9S)-N-[(3',6'-dihydroxy-3-oxospiro [isobenzofuran-1(3H),9'-[9H]xanthen]-5yl) methyl]-4-[(9-hydroxycinchonan-6'-yl)oxy]butamide (7) bears a neutral charge on the molecule, in contrast, tracer (14) has a positive charge on the quinuclidine ring. The new tracer is highly stable at 37° C. as shown in FIG. 8, an important property for the performance of the tracer in the FPIA assay. An accelerated stability study conducted at 45° C. for 4 weeks demonstrated no loss of curve span (see FIG. 7). The C-6 tracer also performed well with MoAb Q6-6C5. The tracer-antibody pair exhibited a large dynamic curve span (204 mP) demonstrating a better precision and sensitivity in the measurements of analytes over a known tracer compound (14) (151 mP), as shown in FIG. 6.

FIG. 8 illustrates the comparison in the performance in the FPIA between the new C-6 tracer (7) and MoAb Q6-6C5 pair of the present invention and a tracer and antibody pair from a commercially available FPIA kit for quinidine (TDx, Abbott Laboratories). The standard curve shown in FIG. 8 indicates that the tracer of the present invention (7) has a larger dynamic span than that obtained with the TDx assay, therefore demonstrating better sensitivity and precision in measurement of quinidine.

Figure 3:
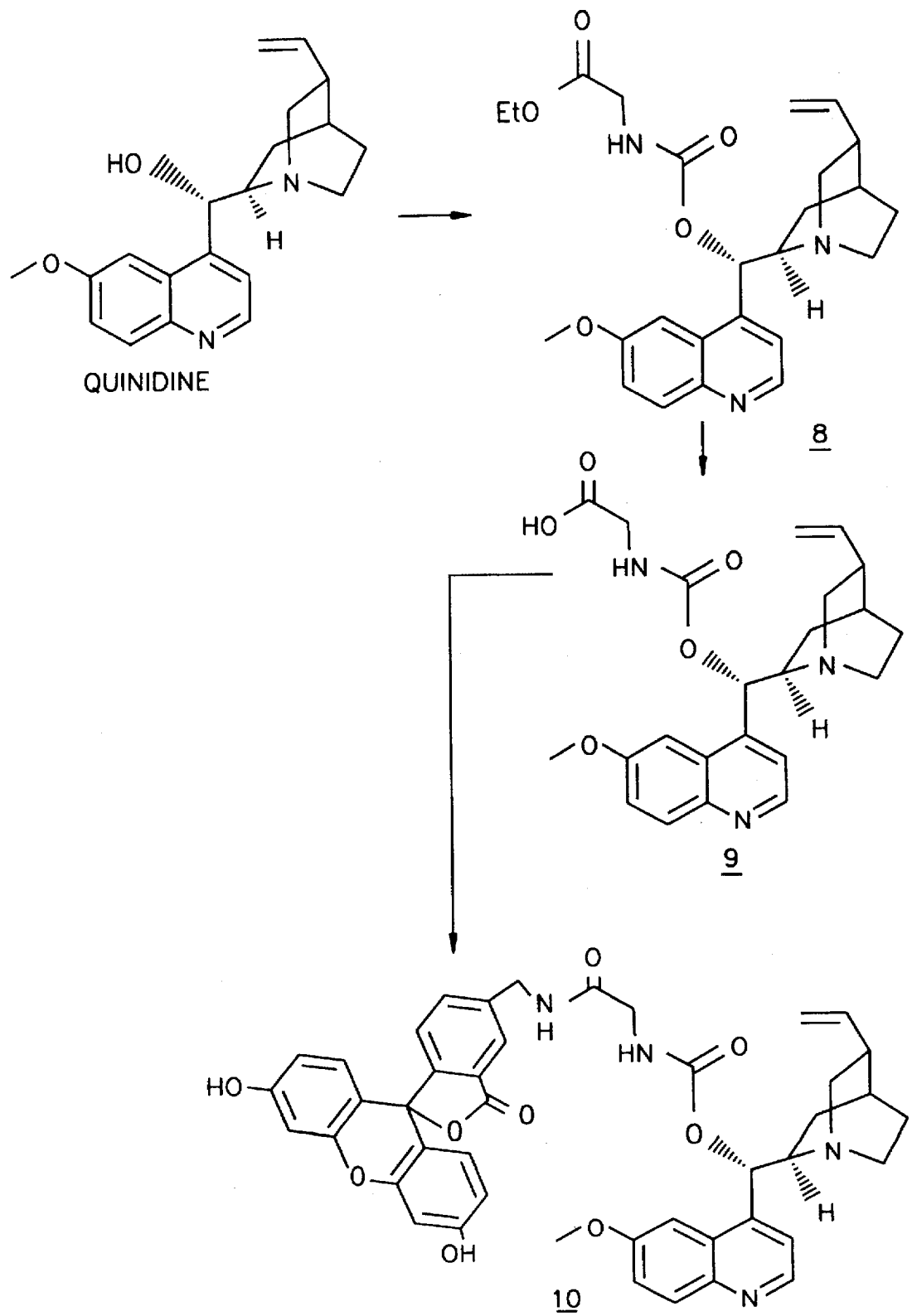
FIG. 3 shows the formulae of the starting materials and intermediates involved in the synthesis of (9S)-[2-[[(3',6'-Dihydroxy-3-oxospiro[isobenzofuran-1(3H),9'-[9H]pantheon]-5-yl) methylamino]-2-oxoethyl]carbamic acid 6'-methoxycinchonan-9-yl ester (10)

Tracers synthesized out of an alternate position on the quinidine molecule, for example the C-9 position can be prepared. FIG. 3 illustrates the method of preparing the C-9 tracer (9S)-[2-[[(3',6'-Dihydroxy-3 -oxospiro [isobenzofuran-1(3H),9'-[9H]pantheon]-5-yl) methylamino] -2-oxoethyl]carbamic acid 6'-methoxycinchonan-9-yl ester (10). Quinidine is treated with ethylisocyanatoacetate at room temperature to give the carbamate ester (8). The ester (8) is hydrolyzed to provide the corresponding acid (9). The acid (9) is converted to the active ester by reaction with dicyclohexyl carbodiimide and N-hydroxysuccinimide followed by coupling with 5-aminomethyl fluorescein in pyridine to give the C-9 quinidine tracer (10). The synthesis is further detailed in Examples 14-16.

However, when tested in the FP immunoassay, the C-9 (10) tracer did not bind to the preferred quinidine antibody MoAb Q6-6C5. Table 2 demonstrates the binding ability of the monoclonal antibody MoAb Q6-6C5 to the C-6 and C-9 tracers. The ability of binding is expressed as the degree to which polarization is retained by the antigen-antibody complex as indicated in mP units. As Table II below indicates, increasing the concentration of MoAb Q6-6C5 to 1:20 titer had no effect on the C-9 tracer. hence no binding of tracer to the antibody, and no standard curve could be generated. In comparison, the tracer derived out of the C-6 position showed good binding to the monoclonal antibody and a high degree of polarization that is retained.

TABLE 2

COMPARISON C-6 (7) TRACER vs C-9 (10) FP TRACER ON MOAB Q6-6C5

| MoAb Q6-6C5, titer | (C-9 tracer) | (C-6 tracer) |
|---|---|---|
| 1:20 | 28.6 mP | — |
| 1:40 | 25.3 mP | — |
| 1:525 | — | 240 mP |
| 1:550 | — | 238 mP |

As demonstrated by the results in Table 2, it is important to the performance of the FPIA to have both the antibody and tracer produced from compounds which were derived from the C-6 position on the quinidine molecule.

Fluorescein molecules other than aminomethylfluorescein can be used to prepare the novel quinidine fluorescence polarization tracers of the present invention. The use of 5-carboxyfluorescein has been shown in other FPIAs (see U.S. Pat. No. 4,668,640). However, extensive modification of quinidine is required to introduce an amino linker arm for effectively linking the quinidine to the carboxyfluorescein. Methodology to make a carboxyfluorescein labeled quinidine derivative out of the C-6 position has not been published.

A preferred carboxy-fluoroscein tracer of the present invention has the formula

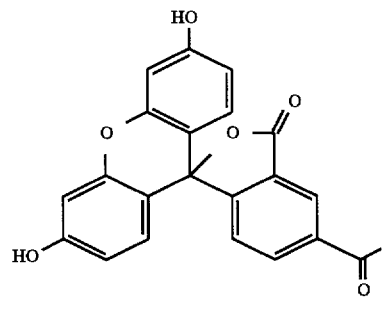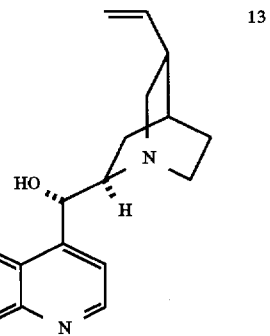

Figure 4:
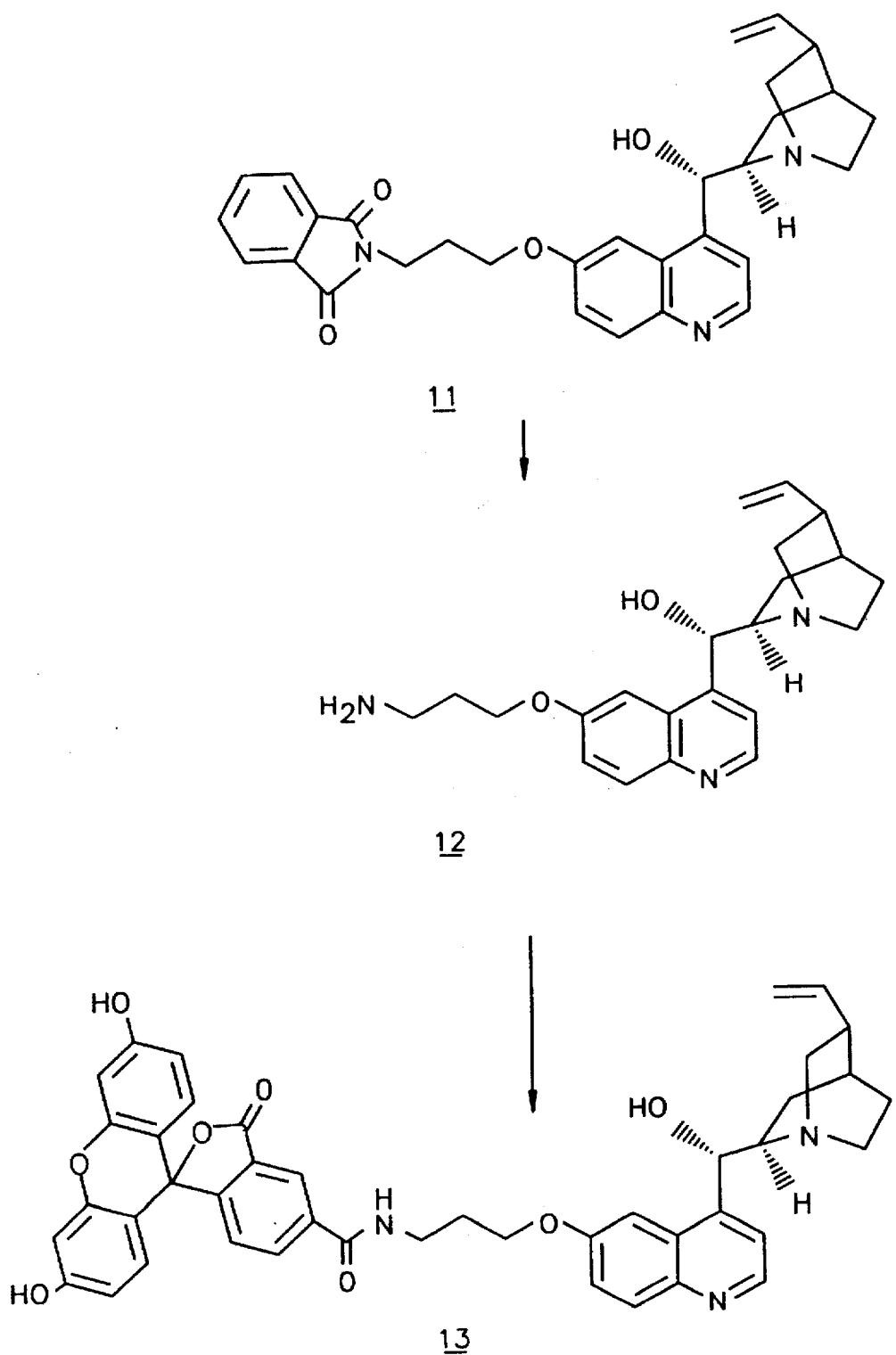
FIG. 4 shows the formulae and starting materials involved in the synthesis of (9S)-3',6'-Dihydroxy-N-[3-(9-hydroxycinchonan-6'-yl) oxy]propyl]-3-oxospiro [isobenzofuran-1 (3H), 9'-[9H]xanthene]-5-carboxamide (13)

FIG. 4 illustrates the general method for preparing the (9S)-3',6'-Dihydroxy-N-[3-[(9-hydroxycinchonan-6'-yl)oxy]propyl]-3-oxospiro[isobenzofuran-1 (3H), 9'-[9H]xanthene]-5-carboxamide (13) and Examples 17–19 provide the synthesis of the compound.

The carboxyfluorescein tracer (13) used in the FPIA with the polyclonal antibody P796 derived from the same quinidine immunogen used to prepare MoAb Q6-6C5 demonstrated a good dynamic span (e.g. >150 mP). The data shown in Table 3 demonstrate that the carboxyfluorescein tracer is stable at 37° C. and performs well in the assay.

TABLE 3

Quinidine polyclonal antibody and carboxy tracer (13) stability (mP units).

| ug/mL | Day 0 | 37° C. 1 week | 37° C. 4 week | 37° C. 6 week |
|---|---|---|---|---|
| 0 | 239.4 | 236.9 | 234.9 | 232.4 |
| 0.5 | 229.8 | 214.7 | 207.8 | 200.7 |
| 1 | 198 | 181.2 | 171 | 168.9 |

TABLE 3-continued

Quinidine polyclonal antibody and carboxy tracer (13) stability (mP units).

| ug/mL | Day 0 | 37° C. 1 week | 37° C. 4 week | 37° C. 6 week |
|---|---|---|---|---|
| 2 | 131.4 | 119.8 | 115.5 | 118.2 |
| 4 | 95.6 | 93 | 94.3 | 94.5 |
| 8 | 77.3 | 77.1 | 78.5 | 79.4 |

The novels tracers and antibody of the present invention can be provided in an immunoassay kit for the determination of quinidine amounts in sample body fluids such as serum. In a preferred embodiment the kit will be used for performing the immunoassay on the automated COBAS FARA II® chemistry system (COBAS FP assay system, Roche Diagnostics, Inc., Somerville, N.J.) A kit for performing a flourescence polarization immunoassay to determine the concentration of quinidine in human serum comprises a tracer compound of formula IV, for example compound 7 or 13, and an antibody, for example MoAb Q6-6C5, generated from a compound of formula II.

EXAMPLES

The following are non-limiting examples which illustrate the synthesis of the novel quinidine derivatives of the present invention and the use of these compounds in a fluorescence polarization immunoassay system. The numerical designations of the compounds in the headings and in Examples 1–19 refer to the structural formulae shown in FIGS. 1 through 4.

The chemical structures of the intermediates and final product of the synthesis of (9S)-4-[(9-hydroxycinchonan-6'-yl)oxy]-1-iminobutyl-[BTG] (4) are shown in FIG. 1. The chemical structures of the intermediates and final product of the synthesis of (9S)-N-[(3',6'-dihydroxy-3-oxospiro[isobenzofuran-1(3H),9'-[9H]xanthen]-5yl) methyl]-4-[(9-hydroxycinchonan-6'-yl)oxy]butamide (7) are shown in FIG. 2. The chemical structures of the intermediates and final product of the synthesis of (9S)-[2-[[(3',6'-Dihydroxy-3-oxospiro[isobenzofuran-1(3H),9'-[9H]pantheon]-5-yl) methylamino]-2-oxoethyl]carbamic acid 6'-methoxycinchonan-9-yl ester (10) are shown in FIG. 3. The chemical structures of the intermediates and final product of the synthesis of (9S)-3',6'-Dihydroxy-N-[3-[(9-hydroxycinchonan-6'-yl) oxy]propyl]-3-oxospiro [isobenzofuran-1 (3H), 9'-[9H]xanthene]-5-carboxamide (13) are shown in FIG. 4.

Example 1

Preparation of 6-Hydroxycinchonine(1).

A 1l three-necked, round-bottom flask equipped with a condenser under argon atmosphere was charged with 5.0 g (15.4 mmol) of quinidine (97%, Aldrich) and 500 ml of dichloromethane. The solution in the flask was cooled to −78° C. To this cooled solution was slowly added 61 ml (61 mmol) of 1.0M borontribromide in dichloromethane over a period of 45 minutes. The reaction mixture was allowed to warm up to room temperature for a period of 2.5 h and was heated to reflux for 1 h. The reaction flask was cooled to −20° C. and 115 ml of 10% aqueous sodium hydroxide was slowly added. During the addition the temperature of the reaction mixture was maintained at 0° C. and was stirred vigorously. The mixture was transferred into a 2 l separatory funnel. The remaining residue in the flask was transferred into the separatory funnel with the aid of a mixture of 5 ml of 10% sodium hydroxide and 20 ml of dichloromethane. The mixture in the separatory funnel, which contained some gummy yellow semi-solid, was shaken vigorously for 10 minutes and the aqueous layer was allowed to separate slowly from the organic phase. The organic layer was discarded and the aqueous phase was washed with 100 ml of dichloromethane and was cooled to 0° C. To the aqueous phase was added 12.5 ml of concentrated hydrochloric acid (HCl). This pH of this solution was adjusted to pH 10 with concentrated ammonium hydroxide. The resulting mixture was extracted with 12×250 ml of chloroform, dried with anhydrous sodium sulphate, concentrated and yielded 3.1 g of 6-hydroxycinchonine (1). The mother aqueous layer was extracted with 2×200 ml of n-butanol and yielded an additional 1.0 g to provide a total yield of 4.1 g of 6-hydroxycinchonine (1) (13.2 mmol, 86%). MS, IR and NMR data confirmed the identity of the compound.

Example 2

Preparation of (9S)-4-[(9-Hydroxycinchonan-6'-yl)oxy] butanenitrile(2).

To a solution of 400 mg (1.2 mmol) of 6-hydroxycinchonane (1) in 25 ml of anhydrous acetone (dried and distilled over potassium carbonate) and 5 ml of anhydrous dimethylformamide was added 267 mg (1.93 mmol) of anhydrous potassium carbonate followed by 129 ml (0.87 mmol) of 4-bromobutyronitrile and a catalytic amount (3 mg) of 18-crown-6. The reaction mixture was heated to reflux for 18 h, cooled and filtered. The filtrate was concentrated under reduced pressure and redissolved in 200 ml of chloroform. The organic layer was washed with 2×50 ml of 5% aqueous sodium hydroxide, washed with brine, dried using anhydrous magnesium sulfate and yielded 310 mg (0.82 mmol, 66%) of (9S)-4-[(9-hydroxycinchonan-6'-yl)oxy]butanenitrile (2) as pale yellow solids. MS, IR and NMR data confirmed the identity of the compound.

Example 3

Preparation of (9S)-4-[(9-hydroxycinchonan-6'-yl) butanimidic acid methyl ester (3).

Hydrochloric acid gas was bubbled through a solution of 200 mg (0.52 mmol) of (9S)-4-[(9-hydroxycinchonan-6'-yl) oxy]butanenitrile (2) in 5 ml of anhydrous methanol at −10° C. for a period of 15 minutes. The reaction mixture was stoppered and left at 4° C. for 4 days, concentrated to dryness and yielded 220 mg (0.49 mmol, 93%) of (9S)-4-[ (9-hydroxycinchonan-6'-yl)butanimidic acid methyl ester (3) as solids. HNMR indicated the purity of (9S)-4-[(9-Hydroxycinchonan-6'-yl)butanimidic acid methyl ester (3) was 75% with the remaining 25% as the hydrolyzed compound.

Example 4

Preparation of 9(S)-6'-Cyanomethyloxy cinchonane-9-ol (wherein L=1).

To a solution of 0.5 g (1.59 mmole) of 6'-hydroxycinchonine and 5 ml of dry DMSO is added slowly over a period of 0.5 h 2.0 ml of n-butyl lithium (1.6M/hexane, Aldrich). The reaction flask is cooled in an ice bath and then treated with 96 mg (1.27 mmole) of chloroacetonitrile. The temperature of the reaction mixture is allowed to rise to room temperature over a period of 2 h and the mixture is stirred for 1 h at room temperature. The reaction mixture is poured into 25 ml of deionized water and 5 ml of ethyl acetate during which some of the product oils out. 100 ml of dichloromethane is added to dissolve the oily product and produce two layers. The heterogeneous brown mixture is concentrated under reduced pressure to remove the organic solvents during which the product precipitates. The mixture is left to stand overnight in the refrigerator. The precipitate is collected and washed with ETOAc to yield an off-white solid, 0.4 g.

Example 5

Preparation of 6'-Cyanoethyloxy cinchonine (wherein L=2).

To a solution of 0.5 g (1.59 mmol) of 6-hydroxycinchonine in 25 ml of anhydrous acetone (dried and distilled over potassium carbonate) and 5 ml of anhydrous dimethylformamide is added 0.329 g (2.39 mmol) of anhydrous potassium carbonate followed by 0.142 g (1.59 mmol) of 3-chloropropionitrile (Aldrich) and 3 mg of 18-crown-6. The reaction mixture is heated to reflux for 18 h, cooled and filtered. The filtrate is concentrated under reduced pressure and redissolved in 200 ml of chloroform. The organic layer is washed with 2×50ml of 5% aqueous sodium hydroxide, washed with brine and dried using anhydrous magnesium sulphate to yield 0.415 g (1.13 mmol, 71%) of 6'-cyanoethyloxy cinchonine as pale yellow solids.

Example 6

(9S)-6'-(3-Cyanobenzyloxy) cinchonane-9-ol (wherein L=benzyl).

To a solution of 0.6 g (1.91 mmol) of 6-hydroxycinchonine in 25 ml of anhydrous acetone (dried and distilled over potassium carbonate) and 8 ml of anhydrous dimethylformamide is added 0.516 g (2.87 mmol) of anhydrous potassium carbonate followed by 0.329 g (1.91 mmol) of 3-(bromomethyl)benzonitrile (Lancaster) and 4 mg of 18-crown-6. The reaction mixture is heated to reflux for 18 h, cooled and filtered. The filtrate is concentrated under reduced pressure and redissolved in 200 ml of chloroform. The organic layer is washed with 2×50 ml of 5% aqueous sodium hydroxide, washed with brine, dried with anhydrous magnesium sulphate to yield 0.647 g (1.51 mmol, 79%) of (9S)-6'-(3-cyanobenzyloxy) cinchonane-9-ol as pale off-white solids.

Example 7

Preparation of quinidine immunogen (9S)-4-[(9-hydroxycinchonan-6'yl)oxy]-1-iminobutyl-[BTG] (4).

A freshly prepared solution of 166 mg of compound (9S)-4-[(9-hydroxycinchonan-6'-yl)butanimidic acid methyl ester (3) in 1 ml of dry DMSO was added rapidly to a solution mixture of 55.5 ml of DMSO and 0.1M potassium phosphate (KPi) pH 7.5 (3:1) containing 700 mg of bovine thyroglobulin (BTG). The reaction mixture was stirred overnight at 4° C. The resulting conjugate was placed in a dialysis tube (50,000 MW cut-off) and was dialyzed in a 3:1 mixture of DMSO/50 mM KPi pH 7.5, 1:1 mixture of DMSO/50 mM KPi pH 7.5, 1:3 mixture of DMSO/50 mM KPi pH 7.5, and twice in 50 mM KPi buffer pH 7.5. The conjugate was removed and sterile filtered to yield 110 ml solution of 6.5 mg/ml as determined by protein assay (Coomasie Blue). The degree of lysine modification of this conjugate was determined by the ability of the remaining lysine residues to react with trinitrobenzenesulfonic acid (TNBS). The resulting yellow complex was then measured at 420 nm. The results indicated that 63% of the available lysines in the quinidine immunogen had been modified. This material was used for animal immunization.

Example 8

Preparation of quinidine-bovine serum albumin (BSA) conjugate (9S)-4-[(9-hydroxycinchonan-6'yl)oxy]-1-iminobutyl-[BSA].

To a solution of BSA (1.2 g in 19 ml of 0.1M (KPi) pH 7.5) containing 57 ml of DMSO was added rapidly a freshly prepared solution of (9S)-4-[(9-hydroxycinchonan-6'-yl) butanimidic acid methyl ester (3) (23 mg in 1 ml of dry DMSO). The reaction was stirred overnight at 4° C. The resulting conjugate was placed in a dialysis tube (10,000 MW cut-off) and was dialyzed in a 3:1 mixture of DMSO/50 mM KPi pH 7.5, 1:1 mixture of DMSO/50 mM KPi pH 7.5, 1:3 mixture of DMSO/50 mM KPi pH 7.5, and twice in 50 mM KPi buffer pH 7.5. The conjugate was removed, sterile filtered and yielded a 115 ml solution of 10.2 mg/ml as determined by protein assay (Coomasie Blue). This material served as the conjugate-capture for the antibody screening by ELISA.

Example 9

Preparation of disubstituted quinidine derivative (S)-8-ethenyl-2-[hydroxy-6-(2-ethoxy-2-oxoethoxy)-4-quinolinylmethyl]-1-(2-ethoxy-2-oxoethyl)azoniabicyclo[2.2.2]octane iodide (15).

A 1-l 3-necked, round-bottomed flask equipped with a magnetic stirrer was charged with 2.0 g (6.44 mol) of 6-hydroxycinchonine (1) and 10 ml of DMSO which had been dried over molecular sieves. To the stirred solution was added very slowly over a period of 0.5 h 2.8 ml (7.0 mmol) of n-butyl lithium (2.5M/hexane, Aldrich). The reaction flask was cooled with an ice-water bath and then treated with 1.6 ml (13.57 mmol) of ethyl iodoacetate. The temperature was allowed to rise to room temperature over a period of 2 h and the mixture was stirred at room temperature for 1 h. The reaction mixture was poured into 65 ml of deionized water and 15 ml of ethyl acetate during which some of the product oiled out. 100 ml of dichloromethane was added to dissolve the oily product and produce two layers. The heterogeneous brown mixture was concentrated under reduced pressure to remove the organic solvents during which the product precipitated. The mixture was left to stand overnight in the refrigerator. The precipitate was collected and washed with ETOAc and yielded 1.6 g (41%) of (S)-8-ethenyl-2-[hydroxy-6-(2-ethoxy-2-oxoethoxy)-4-quinolinylmethyl]-1-(2-ethoxy-2-oxoethyl)azoniabicyclo[2.2.2]octane iodide as an off-white solid. NMR, IR and MS data confirmed compound identity.

Example 10

Preparation of disubstituted quinidine derivative (9S)-1-(3-carboxypropyl)-6'-(3-carboxypropoxy) cinchoninum chloride (16).

To a solution of 2.7 g (8.7 mmol) of (1) in 75 ml of dry acetone (dried and distilled over potassium carbonate) and 25 ml of dimethylformamide (Aldrich, 99%) was added 2.5 g (18.1 mmol) of anhydrous potassium carbonate, followed by 2.49 ml (17.4 mmol), of ethyl-4-bromobutyrate and 25 mg of 18-crown 6. The reaction mixture was heated under reflux for 18 h, cooled, filtered and the filtrate was concentrated under reduced pressure. The residue was purified by silica gel column chromatography using a mixture of 6:1:1:1 ethyl acetate:methanol:water:acetone as the eluent to give 2.7 g of diethylester as a brown oil. This oil was treated with 1.4 g of potassium carbonate in 150 ml of methanol and heated to reflux for 20 h. The reaction mixture was concentrated and redissolved in 15 ml of water. The resulting solution was adjusted to pH 5 with 1N HCl. This was concentrated under reduced pressured and the brown residue was purified on preparative thin layer chromatography using a mixture of 8:1:1 ethyl acetate:methanol:water and yielded 2.34 g (51%) of diacid as off-white powders. MS, IR and NMR data confirmed the identity of the compound Example 11

Preparation of (9S)-4-[(9-Hydroxycinchonan-6'-yl) oxybutanoic acid ethyl ester (5).

To a solution of 250 mg (0.80 mmol) of (1) in 6 ml of dry dimethylformamide (Aldrich, 99%) was added 110 mg (0.80 mmol) of anhydrous potassium carbonate, followed by 109 ml (0.75 mmol) of ethyl-4-bromobutyrate and catalytic amount (4 mg) of 18-crown 6. The reaction mixture was heated at 120° C. for 2 h, cooled, and placed under reduced pressure to remove dimethylformamide. 50 ml of dichloromethane was added to the residue and the mixture was filtered. The filtrate was washed with 2×25 ml of 5% sodium hydroxide, brine, dried (anhydrous sodium sulphate) and concentrated. The residue was purified on preparative thin layer chromatography using a mixture of 6:1:1:1 ethyl acetate:methanol:water:concentrated ammonium hydroxide as the eluent and yielded 160 mg (0.37 mmol, 45%) of (5) as brown oil. MS, IR and NMR data confirmed the identity of the compound.

Example 12

Preparation of (9S)-4-[9-Hydroxycinchonan-6'-yl) oxybutanoic acid(6).

A mixture of 150 mg (0.35 mmol) of (5) and 80 mg of potassium carbonate in 35 ml of methanol was heated to reflux for 20 h. The reaction mixture was concentrated and redissolved in 15 ml of water. The resulting solution was adjusted to pH 5 with the addition of 1N HCl. This was concentrated under reduced pressure and the brown residue was purified on preparative thin layer chromatography using a mixture of 8:1:1 ethyl acetate:methanol:water and yielded 85 mg (0.21 mol, 61%) of (6) as off-white powders. MS, IR and NMR data confirmed compound identity.

Example 13

Preparation of (9S)-N-[(3',6'-dihydroxy-3-oxospiro [isobenzofuran-1(3H),9'-[9H]xanthen]-5yl) methyl]-4-[(9-hydroxycinchonan-6'-yl)oxy]butamide (7).

To 50 mg (0.12 mmol) of (6) was added 5 ml of dimethylformamide. After cooling to 0° C., to the resulting solution was added 30 mg (0.14 mmol) of dicyclohexylcarbodiimide and 25 mg (0.21 mmol) of N-hydroxysuccinimide. The mixture was allowed to stir at 4° C. for 48 h and set aside. In another flask was added 60 mg (0.15 mmol) of 5-aminomethyl-fluorescein, hydrochloride and 3 ml of pyridine at room temperature. The precipitate of pyridine hydrochloride immediately appeared. To this suspension was added dropwise the previously prepared N-hydroxysuccinimide solution. The mixture was allowed to stir at room temperature for 4 days and then was concentrated under reduced pressure. The residue was purified on preparative thin layer chromatography (silica, 2 mm) using a mixture of 9:1 ethyl acetate:methanol as the eluent. The orange product obtained indicated the presence of impurities and was repurified on thin layer chromatography (silica, 0.25 mm) using a mixture of 5:1 chloroform:methanol and yielded 24 mg (0.032 mmol, 26%) of (7). MS, IR and NMR data confirmed compound identity.

Example 14

Preparation of (9S)-[[[(6'-methoxycinchonan-9-yl)oxy] carbonyl]amino]acetic acid ethyl ester (8).

To a solution of 200 mg (0.61 mmol) of quinidine in 5 ml of dry dichloromethane was added 74 ml (0.65 mmol) of ethylisocyanatoacetate. The mixture was allowed to stir magnetically at room temperature for 18 h and concentrated under reduced pressure. The residue was purified on preparative thin layer chromatography (silica, 2 mm) using a mixture of 1:9 ethyl acetate:methanol as the eluent and yielded 130 mg (0.28 mmol, 46%) of (8). MS, IR and NMR data confirmed identity of the compound.

Example 15

Preparation of (9S)-[[[(6'-methoxycinchonan-9-yl) oxy] carbonyl]amino]acetic acid (9).

A solution of 120 mg (0.26 mmol) of (8) in 2 ml of methanol was added 200 mg of potassium carbonate and 0.5 ml of water. The mixture was heated to reflux for 2 h and cooled to room temperature. The reaction mixture was filtered and the filtrate was concentrated to remove methanol. The residue was redissolved in 2 ml of water and 1N HCl was added dropwise to the solution until the pH reached 7. The aqueous solution was concentrated, 100 ml of methanol was added and filtered. The filtrate was concentrated and yielded 95 mg (0.22 mmol, 85%) of (9).

Example 16

Preparation of (9S)-[2-[[(3',6'-dihydroxy-3-oxospiro [isobenzofuran-1(3H),9'-[9H]pantheon]-5-yl) methylamino] -2-oxoethyl] carbamic acid 6'-methoxycinchonan-9-yl ester (10).

A solution of 26 mg (0.061 mmol) of (9) in 0.5 ml of dimethylformamide was cooled to 0° C. To the solution was added 20 mg (0.096 mmol) of DCC and 16 mg (0.0139 mmol) of N-hydroxysuccinimide. The reaction mixture was stirred at 4° C. for 20 h and set aside. In another flask was added 30 mg (0.075 mmol) of 5-aminomethylfluorescein hydrochloride and 3 ml of anhydrous pyridine. A precipitate of pyridine hydrochloride formed. To this suspension was added dropwise the previously prepared (in situ) solution of N-hydroxysuccinimide ester. The reaction mixture was allowed to stir at room temperature for 48 h and concentrated under reduced pressure. The residue was applied to preparative thin layer chromatography (silica, 2 mm). The plates were developed using a mixture of 8:2 chloroform-:methanol as the eluent. The yellow product obtained was repurified using the above eluent and yielded 11 mg (0.014 mmol, 24%) of (10) as orange solids. MS, IR and NMR data confirmed the identity of the compound.

Example 17

Preparation of (9S)-2-[3-[(9-hydroxycinchonan-6'-yl) oxy]propyl]-1H-isoindole-1,3(2H)-dione (11).

A mixture of 6-hydroxycinchonine (1) (2.5 g, 8.06 mmol), N-(3-bromopropyl)phthalimide (2.16 g, 8.06 mmol), anhydrous potassium carbonate (1.3 g, 9.4 mmol) and 18-crown-6 (5 mg) in 75 ml of dry acetone was allowed to reflux for 16 h under argon atmosphere. The reaction was cooled to room temperature and 30 ml of methanol was added to make a homogeneous solution. The resulting solution was concentrated and the residue was partially purified on silica gel column chromatography using 5% methanol in chloroform as the eluent. This product was repurified on silica gel column chromatography using 10% methanol in chloroform and yielded 1.08 g (2.17 mmol, 27%) of (11) as off-white solids. MS, IR and NMR data confirmed compound identity.

Example 18

Preparation of (9S)-6'-(3-aminopropoxy) cinchoninan-9-ol (12).

To 300 mg (0.60 mmol) of the quinidine propyl phthalimide (11) was added 2 ml of methyl amine in methanol saturated with gaseous methyl amine. The reaction flask was stoppered and the mixture was allowed to stir at room temperature for 16 h. An aliquot of the reaction mixture was monitored by thin layer chromatography (10% methanol in dichloromethane) and indicated the complete disappearance of starting material. The reaction mixture was concentrated and the residue was redissolved in 30 ml of dichloromethane. The organic layer was extracted twice with an equal volume of water. The aqueous portion was concentrated and yielded 124 mg (0.33 mmol, 56%) of (12) as a clear oil. MS, IR and NMR data confirmed compound identity.

Example 19

Preparation of (9S)-3',6'-dihydroxy-N-[3-[(9-hydroxycinchonan-6'-yl) oxy]propyl]-3-oxospiro [isobenzofuran-1 (3H), 9'-[9H]xanthene]-5-carboxamide (13).

A mixture of 36 mg (0.097 mmol) of the quinidine propylamine (12) and 5-carboxyfluorescein N-hydroxysuccinimide ester (37 mg, 0.098 mmol) in 2.5 ml of dry pyridine was allowed to stir magnetically at room temperature for 3 days under argon atmosphere. The reaction was monitored by thin layer chromatography (8:1:1 ethyl acetate:methanol:water), which indicated the presence of substantial quantities of starting materials. This was then heated between 40°–45° C. for 3 days under argon atmosphere. The mixture was cooled to room temperature and concentrated under reduced pressure. The residue was purified on silica gel column chromatography using 8:1:1 ethyl acetate:methanol:water as the eluent and yielded 4 mg (5.5×10−3 mmol, 5.6%) of (13) as orange solids. MS, IR and NMR data confirmed compound identity.

Example 20

Production of polyclonal antibody P796.

For production of polyclonal antibody, a sheep and goat were injected with 1 mg each of the immunogen. The first immunization, using complete Freund's Adjuvant, consisted of multiple injections carried out across the back of the animals. After one week, the second immunization containing 1 mg of the immunogen and incomplete Freund's Adjuvant was injected. Injections were repeated at the third and fourth weeks. Thereafter, the animal received a monthly injection of 3 mg of the immunogen. After 6 months the animal was bled, the blood was allowed to clot, the clot was centrifuged at about 3000 rpm for 15–20 minutes and the serum was separated by means of decantation.

Example 21

Production of monoclonal antibody MoAb Q6-6C5.

For production of the monoclonal antibody, the immunogen for quinidine was injected into female Balb/c mice. The first immunization contained complete Freund's Adjuvant and the second immunization contained incomplete Freund's Adjuvant. Spleen cells from the immunized mouse were fused with NSO myeloma cells in a ratio of 4:1 in the presence of polyethylene glycol (PEG) according to a modification procedure of Kohler and Milstein, Nature, 256 495–497(1975). Hydridoma cell culture supernatants containing monoclonal antibody (MoAb) were screened by ELISA method using BSA coated plates and detected with rabbit anti-mouse Ig conjugated to alkaline phosphatase. The final selection of monoclonal antibody Q6-6C5 was achieved by ELISA followed by analysis in the FPIA assay system.

Example 22

Fluorescence polarization immunoassay (FPIA).

The following assay reagents and protocol were used on the automated COBAS FARA II® analyzer configured for fluorescence polarization determinations for quinidine which are given in this application. (Roche Diagnostic Systems Inc., Somerville, N.J., A subsidiary of Hoffmann-La Roche Inc., Nutley, N.J.).

I. Reagent Formulation for Monoclonal Assay:
  a. Tracer reagent.
    50 mM ACES (N-2-acetamido-2-aminoehanesulfonic acid), pH6.5
    0.01% (w/v) bovine gamma globulin
    0.09% (w/v) sodium azide
    Tracer concentration: 6×10-7M
  b. Monoclonal antibody reagent.
    0.1M phosphate, pH7.5
    150 mM sodium chloride
    0.09% sodium azide
    0.05% bovine serum albumin
    Antibody dilution: 1:550 in antibody buffer.
  c. Quinidine calibrator
    0, 0.5, 1, 2, 4, and 8 ug/mL of quinidine in treated normal human serum, 5 mM EDTA with 0.09% sodium azide.
  d. Sample diluent: Cobas FP Sample Dilution Reagent, code 44268

II. Assay protocol

Mixed 2.6 µl sample with 23.4 µl sample diluent. Added 200 µl antibody reagent and read background. Added 30 µl tracer reagent. Incubated for 30 sec. Read fluorescence polarization at 520 nm.

We claim:

1. A kit for performing a fluorescence polarization immunoassay to determine the concentration of quinidine in body fluid samples, said kit comprising the tracer (9S)-N-[3',6'-dihydroxy-3-oxospiro[isobenzofuran-1(3H),9'-[9H]xanthen]5-yl)methyl]-4-[(9-hydroxycinchonan-6'yl)oxy]butamide and antibody MoAb Q6-6C5 prepared by inoculating a host animal with an immunogen of formula

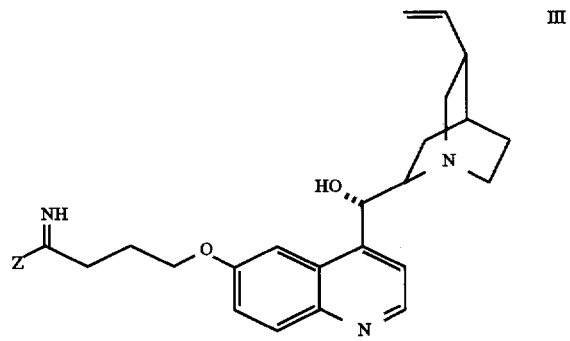

wherein Z is bovine thyroglobulin (BTG), said antibody having a dynamic curve span of at least 150 mP and having a cross reactivity not exceeding the given percentages to the following quinidine metabolite compounds: quinidine-N-oxide 13.5%; 3-S-hydroxyquinidine 11%; 2-oxoquinidine 3%; and O-desmethylquinidine 43.5%.

2. Antibody MoAbQ6-6C5 prepared by inoculating a host animal with the compound of the formula

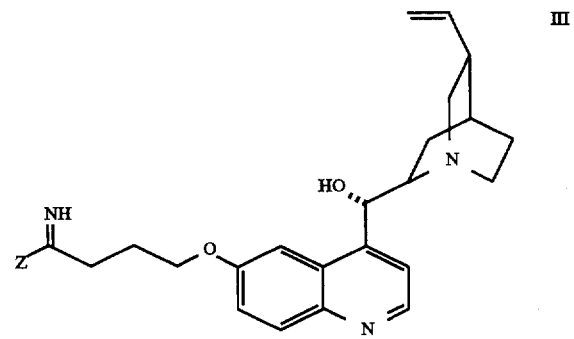

wherein Z is bovine thyroglobulin (BTG), said antibody having a dynamic curve span of at least 150 mP and having a cross reactivity not exceeding the given percentages to the following quinidine metabolite compounds: quinidine-N-oxide 13.5%; 3-S-hydroxyquinidine 11%; 2-oxoquinidine 3%; and O-desmethylquinidine 43.5%.

* * * * *